United States Patent [19]

Gergely

[11] 4,417,993

[45] Nov. 29, 1983

[54] CLEANSING TABLETS FOR TOOTH PROSTHESES

[76] Inventor: Gerhard Gergely, Gartengasse 8, A-1053 Vienna, Austria

[21] Appl. No.: 198,413

[22] Filed: Oct. 20, 1980

[30] Foreign Application Priority Data

Oct. 30, 1979 [AT] Austria ............................... 7005/79

[51] Int. Cl.$^3$ ..................... C11D 7/08; C11D 7/12; C11D 7/18; C11D 17/00
[52] U.S. Cl. ......................................... 252/90; 252/91; 252/99; 252/100; 252/102; 252/103; 252/156; 252/174; 252/174.12; 252/350; 252/DIG. 12; 424/53
[58] Field of Search ............... 252/89.1, 174, 99, 100, 252/102, 174.12, DIG. 12, 90, 156; 424/53

[56] References Cited

U.S. PATENT DOCUMENTS

| | | | |
|---|---|---|---|
| 3,042,621 | 7/1962 | Kirschenbauer | 252/99 |
| 3,042,622 | 7/1962 | Kirschenbauer | 252/99 |
| 3,243,377 | 3/1966 | Stolar et al. | 252/95 X |
| 3,936,385 | 2/1976 | Cheng | 252/99 |
| 3,962,107 | 6/1976 | Levin et al. | 252/95 X |
| 3,997,459 | 12/1976 | Bogie | 252/99 |
| 4,093,417 | 6/1978 | Heinlein | 8/137 |
| 4,234,442 | 11/1980 | Cornelissens | 252/90 |
| 4,256,599 | 3/1981 | Krisp et al. | 252/174 X |
| 4,303,542 | 12/1981 | Heinlein | 252/91 |

FOREIGN PATENT DOCUMENTS 1000628 11/1976 Canada ................................. 252/90

*Primary Examiner*—Dennis L. Albrecht
*Attorney, Agent, or Firm*—Jordan and Hamburg

[57] ABSTRACT

The present invention is directed to an effervescent tablet for cleansing dental prostheses comprising an acidic component and an alkaline component, wherein one of said two components dissolves more slowly than the other component, with the more slowly dissolving component present in stoichiometric excess within the tablet, so that an initial acidic or alkaline pH is provided within the cleansing solution, with the pH gradually adjusting to the opposite alkaline or acidic region as the tablet effervesces.

5 Claims, No Drawings

CLEANSING TABLETS FOR TOOTH PROSTHESES

BACKGROUND OF THE INVENTION

Effervescent tablets for cleaning tooth prostheses are known, consisting substantially of carbonates and/or biocarbonates, solid organic acids as citric acid, tartaric acid and similar materials, phosphates and/or polyphosphates, monosulpho-peracids, wetting agents, binders, cleansing agents, antimicrobials, indicators and other materials.

Furthermore, multilayer effervescent tablets for the cleansing of tooth prostheses are known, in which one layer containing a calcium-binding organic acid initially dissolves, superficially pre-cleansing the prosthesis. The second layer is intended to effect a fine-cleaning or after-cleaning by removing the deposits which are already attacked by the action of the first layer.

All these systems, though, have one disadvantage which will be explained below. It should be kept in mind that the soiling of a prosthesis may be basically divided into three groups as follows:
1. Food scraps of a fatty or fatty-viscous character (desserts, sauces, fruit ices)
2. Adhering proteins (meat, milk product deposits)
3. Poorly soluble mineral deposits arising from saliva (like tartar).

Most cleansing agents for prostheses work very well on group 1, less well on group 2, but almost not at all on group 3. The reason is that wetting agents and oxygen-producing substances are capable of removing fatty substances and combatting development of odors due to decay. However, it is not that easy to remove proteins, which is only possible when the proteins are mixed into the fatty material and can be removed together with it. Most of these methods do not succeed when these proteins strongly adhere to the prosthesis and the prosthesis is badly soiled with such materials. All these methods are completely unsuccessful in connection with tartar-like mineral deposits, which form after long use of a prosthesis without cleansing of a lattice-like substance wherein proteins are deposited.

The known prosthesis cleansing materials principally fail in this instance because tartar deposits can only be dissolved in strongly acidic media and thereby removed. Cleansing of fats and their removal by dispersing agents is logical only at pH's above 7, because cleansing by dispersing agents and particularly splitting off of oxygen at pH's below below 7 are technically not possible.

Thus in principle, are three mechanisms of action needed when it is desired to combat all three causes of soiling when cleansing a prosthesis.

Due to the fact that it is not possible to prepare a cleansing agent which is simultaneously acidic and alkaline, an invention must provide a multi-component tablet within which an acidic and an alkaline component differ in solubility. The purpose of this composition is to keep the pH of the cleansing solution at a preferred, for instance acidic level, initially for a definite time and progressively move the pH into the opposite, alkaline region in order to exert the cleansing power against all three soiling factors.

Here, basically two procedures are possible: the multi-component tablet may begin in the acidic region and after a certain time change into the alkaline region. The other possibility is to regulate the process in the opposite direction, in other words, to begin with alkalinity and thereafter change into the acidic region.

The former procedure is advantageous insofar as the tartar-like mineral deposits are initially dissolved which, due to their micro-crystalline structure, adhere especially strongly to the rough, scratched or mechanically damaged surface of the prosthesis. The easily actuated dissolution of the fatty layer progressively occurs in the alkaline environment.

If sulpho-peracids, dispersing agents, polyphosphates, perborates and similar substances are used for the removal of fatty components, it is also advantageous when these components are the latter ones. It is also advantageous to add in the same time span where this alkalinity is active, cleansing enzymes too, which become active for protracted times after the change from acidic to alkaline reaction. Most cleansing enzymes develop their principal activity in a pH region between 7 and 9 but cleansing enzymes are also known which act in the acidic region.

SUMMARY OF THE INVENTION

Thus the invention relates to a cleansing tablet for dental prostheses containing an acidic-reacting component in an aqueous medium and an alkaline component as components of the effervescent mixture, and preferably included additives, as oxidants, aromatics, coloring material, indicators, antimicrobials, carriers, releasing agents and/or proteolytic enzymes, wherein one of both components, either the alkaline or the acidic component, is more slowly soluble in water relative to the other component, so that the pH is effectively maintained after the addition of the tablet in the alkaline or the acidic region respectively, while simultaneously effervescing, and wherein one of the components is present in a stoichiometric excess in order to adjust the pH of the solution after the end of the reaction of the effervescing mixture into a region of pH opposed to the previously temporarily stabilized pH, in which case a proteolytic enzyme is preferably present in the component which dissolves slower in water and is present in excess.

DETAILED DESCRIPTION OF PREFERRED EMBODIMENTS

Preferably, the more slowly soluble component is the alkaline component in which case the individual component may also contain other conventional neutral or even insoluble additives, particularly those which are intended to be active in that pH region.

According to the invention, there are various possibilities as to the nature of the more slowly soluble component. It may consist of individual more slowly soluble compounds, in which case the words "more slowly soluble" refer to comparison with the other component. A slowly soluble alkali, for example, is anhydrous sodium carbonate. Furthermore, in order to obtain this effect, at least a part of the mass of the previously-mentioned component may be transformed by melting into larger agglomerates and may be comminuted to the desired particle size thereafter so that a slower dissolving rate than the other component is obtain. Salts or compounds may also be used as slower dissolving components which are, due to their nature, hardly soluble or insoluble in water, as for example in the case of the alkaline component, calcium carbonate, calcium hydroxide, magnesium oxide, magnesium hydroxycarbonate and similar compounds, or in the case of the acidic component, fumaric acid, all of which materials aid in the delays which were mentioned before or which will be further explained.

The slow solubility of the respective substances may also be obtained or increased by pressing the materials forming this component with a filler exhibiting slow solubility, as for example, anhydrous sodium sulphate, slowly dissolving polymeric materials, and similar substances.

This process does not result in a coating of the respective substances but in filling in of the interstices within the compact. This mass of filler must be initially leached out so that the dissolving water is apt to dissolve the alkaline or acidic component steadily but slowly. If the aforementioned component were coated, then the other component would begin to dissolve without significant foaming, thereby loosing the cleansing effect of the bubbling gas. Then, after dissolution of the coating, the second substance would suddenly react with the first one and instantly foam, but not foaming continuously as planned with the tablet according to the invention, where right from the beginning one reactable substance openly lies in the slower reacting layer.

The aforementioned term "hardly dissolving to insoluble" refers to the definition according to DAB 7, according to which one part of a slightly soluble substance is soluble in 100 to 1000 parts of solvent (in this case water). DAB 7 defines as practically insoluble, substances in which not more than one part in more than 1000 parts dissolves. As an example of a practically insoluble substance, calcium carbonate with a solubility product of $4.8 \times 10^{-9}$ at 25° C. or magnesium oxide (soluble as hydroxide) of $5.5 \times 10^{-12}$ may be mentioned.

"Polymeric substances dissolving slowly in water" are such polymers which at first soak up water, then as might happen, swell and dissolve only slowly. Examples are colloids or pseudo-colloids as water-soluble proteins, cellulose ethers, cellulose esters, polyvinyl alcohol and similar materials. Due to their availability, it is particularly advantageous to use carboxymethylcellulose, methylcellulose, esters of alginic acid such as the propyl ester, and gelatine. The enumeration of these compounds does not exclude the use of other substances having similar properties, such as slowly dissolving glycerides of vegetable fatty acids instead.

As mentioned before, the cleansing tablet according to the invention may also contain in already-known fashion a cleansing enzyme or proteolytic enzyme. This enzyme though, must be capable of remaining active within the slowly soluble component. Not more than 1% by wt of proteolytic enzyme is preferably added.

The enzyme preferably subsists in a separate, non-effervescing layer. The cleansing tablets according to the invention may also be one-layer tablets or multi-layer tablets. In the case of a one-layer tablet, the more slowly soluble component and the component reacting with it, together with additional components if so needed, are pressed to yield a tablet in which case 1-5% by wt polyvinyl pyrrolidone (calculated) on the whole mass of the tablet) or Carbowax with a molecular weight of 4000 to 20,000 may be used as a binder.

In multi-layer tablets, both phases are found in two layers, and an additional layer may be provided for the enzyme. It is of course also possible to provide the enzyme of a two-layer tablet in the layer of the slowly soluble component.

In a three-layer tablet, the uppermost layer, for instance, contains sodium carbonate, sodium polyphosphate, potassium persulphate, potassium persulphate sodium citrate, sodium bicarbonate, dispersing agents and indicator dyes, and, also if need be, a small amount of acid for the development of gas, without making the solution acidic. The median layer lying underneath contains the proteolytic enzyme embedded in protective substances as anhydrous sodium sulphate and compression adjuvants, as, for instance polyethylene glycol 20,000, polyvinyl pyrrolidone and anhydrous sodium sulphate.

The bottom acidifying layer contains as an acidifying component, for example sulfamic acid, potassium persulphate and dispersing substances. Furthermore, this layer contains a filler as, for example, a vegetable fatty acid glyceride, which reduces the solubility of the acidic component considerably.

Thus such a tablet will create an alkaline environment at the beginning in the aqueous treatment solution, which becomes strongly acidic after the neutralization of the alkaline layer. The enzyme used here must be active in an acidic region.

Other acidifiers may be used too, preferably betaine hydrochloride, and also conventional ingredients as fumaric acid and citric acid.

When it is desired to operate the system in the opposite direction (which is more advantageous, as explained further), it may be constituted as follows.

The uppermost layer of the tablet preferably consists of an effervescent mixture whose carbonate portion is stoichiometrically inferior to the acid portion and where dissolution occurs at a pH of 3 to 5, serving to remove tartar. Fumaric acid, sodium fumarate, sulfamic acid or betaine hydrochloride may be used instead of citric acid. This layer may also contain an indicator and will dissolve the inorganic skeletal substances of tartar-like compositions within 5 to 20 minutes.

The second layer may now consist of an alkali, dissolving slower than the acidic component of the first layer, which again constains conventional products such as potassium persulfate, potassium perborate, sodium polyphosphate, potassium persulfate, dispersants etc. Whereas the first layer acidifies the solution, the second layer neutralizes the acids which previously dissolved tartar and subsequently adjusts the pH of the solution towards an alkaline pH where the dispersants as well as the perborate and the persulfate become active.

In order to improve stability, these layers may be separated, so that, for example, the alkali sensitive persulfates and perborates are embedded in a neutral third layer, while the middle layer only serves to slowly supply a very strong alkali for alkalinization.

Of course one of these two layers or a separate third layer may serve as a carrier for proteolytic enzymes.

The cleansing tablets according to the invention preferably consist of three layers because the performance of a two-layer tablet is greatly affected by the layer of the tablet which lies upon the bottom of the water-filled beaker which is intended to serve in the cleansing process of the prosthesis. In a three-layer tablet, the third and outer layer which carries the enzyme has the function of providing for operation of the system when the tablet falls into the water, so that, for example, the acidic layer, which is initially supposed to dissolve, lies flat upon the bottom of the beaker. In that situation, namely, the third layer carrying the enzyme will lie on top and will, due to its nature and its hard solubility, prevent the extremely rapid dissolution of the second layer from occuring. This happens even though the second (alkaline) layer also dissolves slowly and thereby shortens the desired cleansing effect of the acidic phase. This would happen in a two-layer tablet because the more slowly soluble alkaline layer takes a desirably long period of time for dissolution even when the acidic layer abuts the bottom and also dissolves very slowly. Thus the whole process is adjusted to prevent an initially protracted strongly acidic phase.

The effervescent tablets according to the invention show the additional advantage that, when the alkaline phase is the final phase, i.e., when the alkaline component is the slowly dissolving component and caroate is present as a further tablet component, the effervescing effect will be prolonged after neutralization of the acidic component and adjustment into the distinctly alkaline region, because the persulfate decomposes under generation of oxygen. The more slowly soluble component, therefore, preferably contains a slowly dissolving alkali as, for example, anhydrous sodium carbonate, and sodium persulfate. As has been known for quite some time, the anhydrous sodium carbonate needs to bind water in order to become hydrated and dissolve. Within that period of time, almost no reaction of the potassium persulfate of this layer occurs, so that physical action alone slows down the dissolution of the second layer. Once pH equaling 7 is reached, i.e., after the neutralization of the acid, only the carbonate dissolves and the persulfate decomposes while releasing oxygen. The enzyme present in the third layer may be protected from the generation of oxygen, and last for quite some time in the middle third layer by being embedded in a slowly dissolving neutral salt as sodium sulfate, in which case this layer is furnished with swellable substances of the previously-mentioned type.

With a system of this kind, it is also possible to not only obtain a long lasting acidic and a final alkaline cleaning period, but to also obtain oxygen percolation, lasting from pH equaling 2 into the alkaline region with a pH of 8.5. It is reasonable that a long-lasting minute saturation of the solution with oxygen is considerably more efficient than a short burst of oxygen.

The expert will easily observe that the features of the invention allow for various combinations of the components of the cleansing tablet in order to obtain the desired effect and in order to fulfill the invention. Here, it is entirely essential that at least one acidic or basic compound in the acidic or alkaline component of the tablet dissolves at such a slower speed so that the solution reacts progressively (naturally either acidically or alkalinally) and thereafter adjusts into the opposite pH region. It is clear that for that purpose, the slower dissolving component must be present in a stoichiometric excess.

The tablet preferably contains an indicator dye for illustrating the change of pH from the acidic to the alkaline value or vice versa.

In the case where the alkaline component is the more slowly soluble one, the pH lies preferably below 6.5, and in the case where the acidic component dissolves slower, the pH is preferably above 7.5 initially and thereafter adjusts into the opposite region.

The invention is explained by the following examples. Example 1 describes the preparation of a slowly dissolving acid component.

EXAMPLE 1

A mixture of 40 parts by weight citric acid and 10 parts by weight anhydrous sodium sulfate is melted and allowed to solidify upon a plate. The solidified melt is pulverized down to the desired particle size and exhibits a solubility that is retarded by the reduced surface.

Example 2 describes the preparation of a slowly dissolving alkaline component.

EXAMPLE 2

20 parts by weight anhydrous sodium carbonate are mixed with 5 parts by weight magnesium hydroxycarbonate, granulated together with a solution of 1 part polyvinyl alcohol, and dissolved in 3 parts by weight methylene chloride. The slow solubility of the alkaline component is caused by the diminishing reactivity of sodium carbonate towards acids by the simultaneous presence of the highly alkaline but uneasily soluble magnesium hydroxycarbonate.

The following example describes the delayed delivery of acids and alkalies in tablet mixtures.

EXAMPLE 3

(a) A typical mixture which initially acts alkaline and subsequently acidic consists of: 20 parts by weight sodium carbonate, 25 parts by weight potassium persulfate, 20 parts by weight polyphosphate, 10 parts by weight sodium perborate. This mixture contains coloring material and aromatics. Dyes may be used as indicators, such as the known universal indicator mixtures or litmus.

Various amounts of dispersing agents may be added to both mixtures, usually between 1 and 2%, and may consist of all types of surfactants as, for instance, sodium lauryl sulfate, cetyl ammonium bromide (active in alkaline as well as in acidic regions) and others.

Up to 1% of a proteolytic enzyme can be added, if so desired. 1 to 5% polyvinyl pyrrolidone or Carbowax (molecular weight between 4000 and 20,000) may be used as binders.

(b) The mixture is mixed with 20 to 30 parts by weight of slowly-dissolving acidic component according to example 1 and pressed into tablet form. Furthermore, fumaric acid, either alone or in combination with the component according to example 1 to a respective amount, may be used as the slowly soluble component.

EXAMPLE 4

Typical mixtures for initially reacting acidically, and subsquently alkalinally: (a) 10 parts by weight sodium bicarbonate, 30 parts by weight potassium persulfate, 5 parts by weight sulfamic acid and 10 parts by weight citric acid. In that situation, the addition of 2 to 4 parts by weight cetyl ammonium bromide is particularly advisable. (b) 60 parts by weight of this mixture are mixed with 50 parts by weight of the slowly dissolving alkaline component according to example 2 and pressed into tablets. Suitable mixtures of various components result in delays of pH alteration from 1 to 3 hours.

The following examples describe multi-layer tablets.

In multi-layer tablets the aforememtioned relationships may be simplified by providing both phases in a two-layer tablet or even more advantageously in a three-layer tablet.

The pH-relationships may be delicately regulated in this situation and any desired delay of the pH-change may be obtained at each desired starting pH by appropriate dosage of the individual layers as well as by choosing the individual components.

EXAMPLE 5

1.3 g of mixture according to 3(a) is pressed into a 25 mm tablet and is pressed together with 1.5 g of the mixture according to example 1. The pressing into one tablet improves the delay of pH-change because the alkaline layer effervesces and the acid-contributing layer lets the pH change slowly after 1½ hours.

Tablets operating according to the reversed principle, i.e., tablets where the alkali-contributing layer is delayed, may be produced by pressing mixture together according to example 4a and according to example 2.

EXAMPLE 6

This is an example of a mixture safe for tropical climates:

1st layer: 20 parts by weight polyphosphate, 10 parts by weight sodium perborate and 1-2 parts by weight surfactant are mixed with a suitable binder, as for example 5 parts by weight Carbowax 20,000, and colored according to need. 2nd layer: 1 part by weight proteolytic enzyme is mixed with 10 parts by weight Carbowax 6000. 3rd layer: 20 parts by weight sodium persulfate, 10 parts by weight fumaric acid, and 2 parts by weight cetyl ammonium bromide are granulated with 5 parts by weight polyvinyl pyrrolidone in 5 parts by weight methylene chloride and dried. Method of operation: The first layer with all alkaline components is separated from the third layer with all acidic components by the neutral median layer so that even moisture entering the tablet cannot lead to a reaction. Once the tablet lies in water, the first layer begins to react with the third layer and causes an alkaline pH. The median layer also dissolves and the proteolytic enzymes begin to act. Only when the tablet dissolves further, the delayed fumaric acid participates in the action and causes the pH of the originally alkaline solution to turn acidic.

EXAMPLE 7

1.5 g of a mixture consisting of 75 parts by weight sulfamic acid, 10 parts by weight sodium bicarbonate, 15 parts by weight sodium carbonate, 12 parts by weight sodium persulfate, 2 parts by weight polyethylene glycol (MW=6000) and 2 parts by weight of a surface-active substance such as alkyl aryl sulfonates, fatty acid condensation products or similar materials are introduced into the open bottom die of a tablet press. This initial acidifying layer of a three-layer table is pre-pressed at a pressure of 0.5 to 1 kbar.

1.5 g of a mixture of 10 parts by weight sodium borate, 60 parts by weight sodium carbonate, 1 part surface active substances (as previously), 6 parts by weight sodium pyrophosphate, 50 parts by weight potassium persulfate and 10 parts by weight of a partial glyceride of a fatty acid consisting of natural straight-chain vegetable fatty acids having a chain length between $C_8$ and $C_{12}$, is deposited upon this layer and is also pre-pressed at a pressure between 0.5 and 1 kbar.

The third layer on top of these two layers consists of 0.5 g of a mixture of 40 parts by weight anhydrous sodium sulfate, 3 parts by weight polyvinyl pyrrolidone, 0.1 parts by weight ascorbic acid, 4 parts by weight magnesium stearate and 1 part by weight proteolytic enzyme. After feeding this mixture into the bottom die, the three-layer tablet is pressed at 8 kbar.

When such a tablet is placed in water the following happens.

The first, acidic layer beings to immediately effervesce and brings the water to a pH of 2 to 3 within 10 to 20 seconds. Simultaneously, the third enzyme-containing layer absorbs water whereby the anhydrous sodium sulfate accepts water but is so-to-say obstructed by the highly viscous polyvinyl pyrrolidone. Thereby, the median alkaline layer is greatly protected from dissolving and reacting despite its position (first layer from top to bottom).

When the initial acidic layer is dissolved, after only 10 to 15 minutes, the second alkaline layer beginning to react, raises the pH above 7 (about 20 minutes) and reaches a pH between 8 and 8.5 after 30 minutes.

After approximately one hour, the strongly-delayed third layer begins to dissolve and frees the enzyme while traces of active oxygen still present are eventually destroyed by ascorbic acid.

I claim:

1. An effervescent cleansing tablet for a dental prosthesis comprising a faster dissolving acidic component which is a mixture of sodium bicarbonate, potassium persulfate, sulfamic acid, and citric acid, and
   a slower-dissolving alkaline component which is a mixture of sodium carbonate and magnesium hydroxycarbonate, said alkaline component present in stoichiometric excess within the tablet, said tablet providing an initial acidic pH in solution while effervescing and gradually adjusting to an alkaline pH.

2. The tablet of claim 1 additionally comprising cetyl ammonium bromide in said acidic component and polyvinyl alcohol in said alkaline component.

3. An effervescent cleansing tablet for a dental prosthesis, comprising a faster-dissolving acidic layer comprising a mixture of sulfamic acid, sodium bicarbonate, sodium carbonate, sodium persulfate, polyethylene glycol, and a surface active substance,
   a slower-dissolving alkaline layer comprising a mixture of sodium carbonate, sodium pyrophosphate, potassium persulfate, a surface active substance, and a partial glyceride of a straight-chain vegetable fatty acid of eight to twelve carbon atoms in length, said alkaline layer present in stoichiometric excess over said acidic layer in said tablet, and
   a layer comprising a mixture of anhydrous sodium sulfate, polyvinyl pyrrolidone, ascorbic acid, magnesium stearate, and proteolytic enzyme,
said tablet providing an initial acidic pH in solution while effervescing and gradually adjusting to an alkaline pH.

4. A process for preparing an effervescent cleansing tablet for a dental prosthesis, comprising a distinct, faster-dissolving acidic layer and a distinct, slower-dissolving alkaline layer, which comprises the steps of
   (A) preparing a mixture of sulfamic acid, sodium bicarbonate, sodium carbonate, sodium persulfate, polyethylene glycol and a surface active substance, forming the faster-dissolving acidic component,
   (B) pre-pressing this acidic component (A) in a table press,
   (C) preparing a mixture of sodium carbonate, sodium pyrophosphate, potassium persulfate, a surface active substance, and a partial glyceride of a straight-chain vegetable fatty acid of eight to twelve carbon atoms in length, forming the slower-dissolving alkaline component, (D) depositing said alkaline component (C) onto the pre-pressed acidic component (B), and (E) pressing said two components (D) in a tablet press.

5. A process for preparing an effervescent cleansing tablet comprising a distinct, faster-dissolving acidic layer, a distinct, slower-dissolving alkaline layer, and a distinct enzyme containing layer, comprising the steps of (A) preparing a mixture of ingredients forming the faster-dissolving acidic component, (B) pre-pressing this acidic component (A) in a tablet press, (C) preparing a mixture of ingredients forming the slower-dissolving alkaline component, (D) depositing said alkaline component (C) onto the pre-pressed acidic component (B), (E) pressing said two components (D) in a tablet press, (F) preparing a mixture of anhydrous sodium sulfate, polyvinyl pyrrolidone, ascorbic acid, magnesium stearate, and proteolytic enzyme, (G) depositing said enzyme-containing mixture (F) onto said pre-pressed alkaline component layer (D), and (H) pressing all three components (G) in a tablet press to form a three-layered tablet.

* * * * *